(12) United States Patent
Faldu et al.

(10) Patent No.: US 11,336,285 B2
(45) Date of Patent: May 17, 2022

(54) STACKED INTEGRATED PLATFORM ARCHITECTURE

(71) Applicant: KONIKU INC., San Rafael, CA (US)

(72) Inventors: Vishal Faldu, San Rafael, CA (US); Budhadev Paul Chaudhuri, San Rafael, CA (US); Renaud Renault, San Rafael, CA (US); Oshiorenoya E. Agabi, San Rafael, CA (US)

(*) Notice: Subject to any disclaimer, the term of this patent is extended or adjusted under 35 U.S.C. 154(b) by 0 days.

(21) Appl. No.: 17/266,084

(22) PCT Filed: Aug. 8, 2019

(86) PCT No.: PCT/US2019/045788
§ 371 (c)(1),
(2) Date: Feb. 4, 2021

(87) PCT Pub. No.: WO2020/033753
PCT Pub. Date: Feb. 13, 2020

(65) Prior Publication Data
US 2021/0313987 A1 Oct. 7, 2021

Related U.S. Application Data

(60) Provisional application No. 62/717,270, filed on Aug. 10, 2018.

(51) Int. Cl.
*H03K 19/173* (2006.01)
*G01N 33/483* (2006.01)
*H03K 19/0948* (2006.01)

(52) U.S. Cl.
CPC ..... *H03K 19/1737* (2013.01); *G01N 33/4836* (2013.01); *H03K 19/0948* (2013.01)

(58) Field of Classification Search
None
See application file for complete search history.

(56) References Cited

U.S. PATENT DOCUMENTS

| 10,209,239 B1 | 2/2019 | Hanson et al. |
| 2006/0172279 A1 | 8/2006 | Smela et al. |

(Continued)

FOREIGN PATENT DOCUMENTS

| JP | 2006-61048 A | 3/2006 |
| JP | 2008-529540 A | 8/2008 |

(Continued)

OTHER PUBLICATIONS

USPTO, International Search Report and Written Opinion for Application No. PCT/US19/45788, dated Nov. 29, 2019.

*Primary Examiner* — Jany Richardson
(74) *Attorney, Agent, or Firm* — Perkins Coie LLP

(57) ABSTRACT

Provided herein is a system comprising (1) a microelectrode array (MEA) component comprising an integrated multiplexed (MUX) logic circuit; and (2) a microprocessor, e.g., MOSFET, such as a CMOS, wherein the MEA is in electrical communication with the microprocessor such that signals produced by the microelectrodes are transmitted to the processor through the MUX. The use of a MUX reduces the number of outputs used to communicate signals from multiple microelectrodes to the microprocessor. The two components are removably engageable with each other such that after one or more uses, the engaged MEA can be removed and replaced with a new MEA, without the necessity of disposing the microprocessor.

14 Claims, 4 Drawing Sheets

(56) References Cited

U.S. PATENT DOCUMENTS

| | | | |
|---|---|---|---|
| 2007/0054266 A1 | 3/2007 | Sato et al. | |
| 2014/0114168 A1 | 4/2014 | Block et al. | |
| 2020/0018742 A1* | 1/2020 | Lopez | H03F 3/393 |

FOREIGN PATENT DOCUMENTS

| | | |
|---|---|---|
| JP | 2009-270980 A | 11/2009 |
| JP | 2011-7741 A | 1/2011 |
| JP | 2013-27376 A | 2/2013 |
| WO | 03100057 A1 | 12/2003 |
| WO | 2008017416 A2 | 2/2008 |
| WO | 2016030378 A1 | 3/2016 |
| WO | 2016062729 A1 | 4/2016 |
| WO | 2017015148 A1 | 1/2017 |
| WO | 2018081657 A1 | 5/2018 |
| WO | 2018208332 A2 | 11/2018 |
| WO | 2018237302 A1 | 12/2018 |

* cited by examiner

STACKED INTEGRATED PLATFORM ARCHITECTURE

REFERENCE TO RELATED APPLICATIONS

This application claims the benefit of the priority date of U.S. provisional application 62/717,270, filed Aug. 10, 2018, the contents of which are incorporated herein by reference.

STATEMENT AS TO FEDERALLY SPONSORED RESEARCH

None.

BACKGROUND

Microelectrode arrays (MEAs) are devices that contain a plurality of exposed microelectrodes through which electrical signals can be received or transmitted. Such signals can be received from or transmitted to living cells which, themselves, produce electrical signals, for example, through depolarization of a cell membrane. Accordingly, MEAs can function as an interface between cells in which they are in electrical contact and electronic circuitry that can process the signals. The electronic circuitry can comprise a microprocessor, including, e.g., a MOSFET, such as a CMOS. Signals from each microelectrode must be transmitted from the device to the MOSFET. As the number of microelectrodes increases, connectors or interfaces between the device and the processor can become increasingly complex.

It is important to develop new platforms for signal recording, stimulation, and transduction.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

SUMMARY

Figure 1:
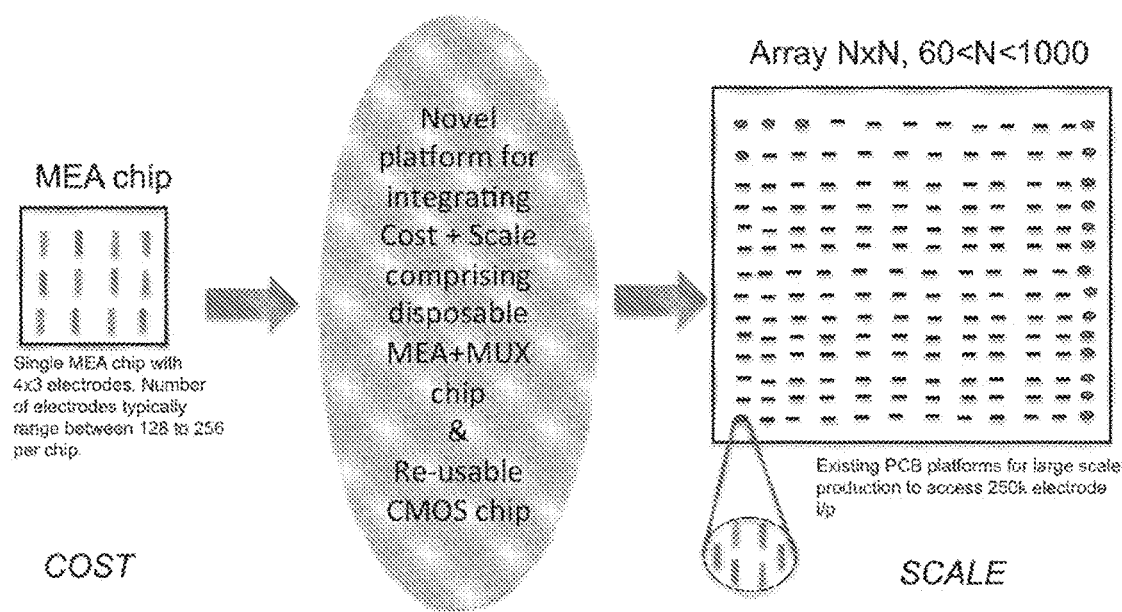
FIG. 1 shows a microelectrode array (MEA) chip with embedded multiplexer (MUX) logic, and a re-usable complementary metal-oxide-semiconductor (CMOS) chip with downstream electronics. The MEA chip may be disposable or replaceable. The MEA chip may be removal or separable from the CMOS chip.

In one aspect provided herein is a system comprising: an microelectrode array (MEA) component comprising an embedded multiplexed (MUX) logic circuit; and a complementary metal-oxide-semiconductor (CMOS) component, wherein said system is configured to: (i) record a signal, (ii) generate a signal, (iii) perform a computational analysis of one or more signals, or (iv) a combination thereof, and wherein said MEA component and said complementary CMOS component are configured to be separable. In one embodiment an electrode of said MEA component is associated with an interfacing component via said MUX logic circuit, and wherein said interfacing component is also associated with said CMOS component. In another embodiment the system further comprises an interfacing component configured to operably connect said MEA component with said CMOS component. In another embodiment said interfacing component comprises an electrical pin, an optical element, or a combination thereof. In another embodiment said interfacing component is configured to align a signal exiting said CMOS component with a receiving portion of said MEA component. In another embodiment MEA component is disposable. In another embodiment said CMOS component is reusable. In another embodiment said MEA component comprises one or more cells. In another embodiment said MEA component comprises at least about 1,000 electrodes. In another embodiment said MEA component comprises at least about 10,000 electrodes. In another embodiment said MEA component comprises at least about 100,000 electrodes. In another embodiment said MEA component comprises at least about 1,000,000 electrodes. In another embodiment said CMOS component performs one or more computations in an absence of an external processor. In another embodiment said MEA component and said CMOS component are configured in a stacked arrangement, wherein a surface of said MEA component is positioned adjacent a surface of said CMOS component. In another embodiment said CMOS component further comprises one or more of the following: a filter, an amplifier, an ADC (analog-to-digital converter), a DAC (digital-to-analog converter), or any combination thereof. In another embodiment said computational analysis comprises: spike signal sorting; a cell, e.g., cell, e.g., neuron, firing rate; an analysis of cell, e.g., neuron, response to a chemical, mechanical, optical, thermal, electrical, or electromagnetic stimulus; or any combination thereof. In another embodiment said MEA component interfaces with one or more cells, e.g., neurons, that express odorant receptors, and said system is configured to perform odorant detection. In another embodiment said system is configured to detect one or more volatile compounds. In another embodiment at least a portion of said system is configured to be implantable in a subject and said MEA component is configured to interface with one or more cells in vivo.

In another aspect provided herein is method comprising: employing the system comprising: an microelectrode array (MEA) component comprising an embedded multiplexed (MUX) logic circuit; and a complementary metal-oxide-semiconductor (CMOS) component, wherein said system is configured to: (i) record a signal, (ii) generate a signal, (iii) perform a computational analysis of one or more signals, or (iv) a combination thereof, and wherein said MEA component and said complementary CMOS component are configured to be separable, to perform odorant detection.

In another aspect provided herein is method comprising: employing the system comprising: an microelectrode array (MEA) component comprising an embedded multiplexed (MUX) logic circuit; and a complementary metal-oxide-semiconductor (CMOS) component, wherein said system is configured to: (i) record a signal, (ii) generate a signal, (iii) perform a computational analysis of one or more signals, or (iv) a combination thereof, and wherein said MEA component and said complementary CMOS component are configured to be separable, to detect one or more volatile compounds.

In another aspect, provided herein is a device comprising a microelectrode array (MEA) comprising a substrate comprising a plurality of microelectrodes in electrical contact with a surface of the substrate, and one or a plurality of multiplexed (MUX) logic circuits integrated with the microelectrode array, each multiplexed logic circuit comprising, (1) as inputs, electrical connections with each of a plurality of the microelectrodes, (2) one or more outputs, and (3) a switch that selects between several input signals and forwards the selected input signal to an output line, wherein the total number of outputs is fewer than the total number of microelectrodes. In one embodiment, the multiplexed logic circuit comprises an integrated circuit. In another embodiment the device further comprises one or more wells or compartments formed on the surface of the substrate, each well or compartment comprising a space in electrical contact with one or a plurality of the microelectrodes. In another embodiment wherein each well comprises one or a plurality of cells. In another embodiment the cells express olfactory receptors. In another embodiment the device comprises a plurality of wells or compartments, wherein each well or compartment comprises a plurality of cells expressing olfactory receptors, wherein the cells in each well or compartment express different olfactory receptors.

In another aspect provided herein is a system comprising: a) a device comprising a microelectrode array (MEA) comprising a substrate comprising a plurality of microelectrodes in electrical contact with a surface of the substrate, and one or a plurality of multiplexed (MUX) logic circuits integrated with the microelectrode array, each multiplexed logic circuit comprising, (1) as inputs, electrical connections with each of a plurality of the microelectrodes, (2) one or more outputs, and (3) a switch that selects between several input signals and forwards the selected input signal to an output line, wherein the total number of outputs is fewer than the total number of microelectrodes; b) an electrical interface configured to engage the one or more outputs; and c) a device comprising a microprocessor, wherein the interface transmits signals from the one or more outputs to the microprocessor. In another embodiment the multiplexed logic circuit draws power from a source outside the MEA device.

In another aspect provided herein is a method comprising: a) engaging a first device comprising a microelectrode array (MEA) comprising a substrate comprising a plurality of microelectrodes in electrical contact with a surface of the substrate, and one or a plurality of multiplexed (MUX) logic circuits integrated with the microelectrode array, each multiplexed logic circuit comprising, (1) as inputs, electrical connections with each of a plurality of the microelectrodes, (2) one or more outputs, and (3) a switch that selects between several input signals and forwards the selected input signal to an output line, wherein the total number of outputs is fewer than the total number of microelectrodes through outputs with an electrical interface configured to transmit signals received from the outputs to a microprocessor; b) receiving and processing electrical signals from the outputs with the microprocessor; and c) disengaging the MEA device from the electrical interface. In one embodiment the method further comprises: d) engaging a second MEA device through outputs with the electrical interface.

In another aspect provided herein is a method comprising: a) providing a system comprising: a) a device comprising a microelectrode array (MEA) comprising a substrate comprising a plurality of microelectrodes in electrical contact with a surface of the substrate, and one or a plurality of multiplexed (MUX) logic circuits integrated with the microelectrode array, each multiplexed logic circuit comprising, (1) as inputs, electrical connections with each of a plurality of the microelectrodes, (2) one or more outputs, and (3) a switch that selects between several input signals and forwards the selected input signal to an output line, wherein the total number of outputs is fewer than the total number of microelectrodes; b) an electrical interface configured to engage the one or more outputs; and c) a device comprising a microprocessor, wherein the interface transmits signals from the one or more outputs to the microprocessor, wherein the microelectrode array device comprises cells in electrical contact with the microelectrodes, which cells produce an electrical signal when exposed to a stimulus; b) exposing the cells to the stimulus to produce an electrical signal; and c) processing electrical signal using the processor. In one embodiment processing comprises determining and intensity of the electrical signal.

In another aspect provided herein is a method of making a device comprising providing a microelectrode array and integrating with the microelectrode array one or more MUX circuits, wherein each MUX circuit receives as input an electrical connection from a plurality of the microelectrodes.

DETAILED DESCRIPTION

I. Introduction

A 3D stacked integrated platform architecture for mass scale CMOS-MEA chip may be designed for signal stimulation, recording and computation. The signal may be a biological signal. The MEA chip may be disposable or replaceable. The MEA chip may be removal from the CMOS chip.

Microelectrode array devices include integrated therewith one or more multiplexers (MUX). The MUX circuits are configured to consolidate inputs from a plurality of microelectrodes in the array into a reduced number of outputs. The outputs are removably connected to a device comprising a processor, such as a MOSFET device, e.g., a CMOS. A geometric arrangement can include a microelectrode array device positioned above a MOSFET device. The outputs can be connected to pins positioned below the microelectrode array device. The pins, in turn, can connect with female headers electrically connected with the processor. The MUX circuits can significantly reduce the number of outputs necessary to transmit signals from the microelectrodes to the processor.

An interface that connects the output of the MEA with the processor can be independent of the two devices or integrated with either, e.g., with a device comprising the processor. The processor can be part of a field programmable gate array. Accordingly, the components can reversibly engage with each other such that an MEA device engaged with a component comprising the processor can be disengaged and replaced with a new MEA. Engaging and disengaging the components can involve engaging and disengaging electrical connections on the MEA with electrical connections in the interface. The interface may comprise pogo pins that engage electrical outputs in the MEA when the MEA is pressed against the pogo pins. Alternatively, pins in the MEA device can mate with female headers connected with the compound comprising the process, e.g., a field programmable gate array. Because the microelectrode array device is removably connected with the processor, the microelectrode array device can be replaced with a new device without having to also replace the processor. Accordingly, a single processor can be used with a plurality of different MEA components.

Existing microelectrode arrays (MEA), made from silicon or glass-like materials, used for biological signal recording, stimulation and transduction, typically have a low number of electrodes ranging from about 4 to about 256 electrodes per chip. Due to the customized and non-standard production techniques followed for manufacture of these MEAs, the manufacturing cost may be typically much higher than traditional semiconductor processing. However, when it comes to downstream signal processing by traditional electronics such as complementary metal-oxide-semiconductor (CMOS) and printed circuit boards (PCBs), the economies of scale may be easily achievable. But as the MEA chip may operate at the intersection of biological fluids, biological matter and semiconductor materials, metal electrodes may undergo degradation over time, causing it to have a limited lifespan.

When the MEA chip is built on top of a CMOS chip, this may necessitate that the entire MEA together with the CMOS chip is discarded once the MEA lifetime has expired. Provided herein is a novel platform combining the benefits of low cost with mass scale production by integrating a MEA chip with embedded multiplexer (MUX) logic, and a re-usable CMOS chip with downstream electronics (See FIG. 1). The MEA chip may be disposable or replaceable. The MEA chip may be removal or separable from the CMOS chip.

Accordingly, provided herein are microelectrode array devices with integrated MUX circuits. Such circuits are capable of drawing power from an external source, such as, a power source that powers a field programmable gate array with which the MEA device is engaged. Because the MEA device is reversibly engageable with the competent comprising the processor, the MEA device is disposable and replaceable on the system.

II. System Level

A novel 3D stacked platform architecture has been designed for cell signal recording, stimulation and subsequent computation. This platform may comprise a microelectrode array (MEA) chip (made either on glass or silicon substrate) with active metal electrodes on the top surface which may be in contact with biological cells (a cell line such as HEK 293 cells, or primary cells such as neurons, or genetically modified cells, etc.) lying in a constrained volume(s) submerged in the appropriate cell media. The MEA chip active area can range from about 2×2 mm2 to about 50×50 mm2. The current state-of-the-art in MEA design involves electrically connecting via pins or wire bonding of MEA electrode outputs to field-programmable gate array (FPGA) and/or CMOS chip. Another variant of this design may be integrating the CMOS and MEA chips on a monolithic structure. However, the disadvantage of these approaches may be the larger footprint of the entire device, which in turn leads to smaller available on-chip area for the active electrodes (since the chip area may be shared between MEA and CMOS regions).

Figure 2:
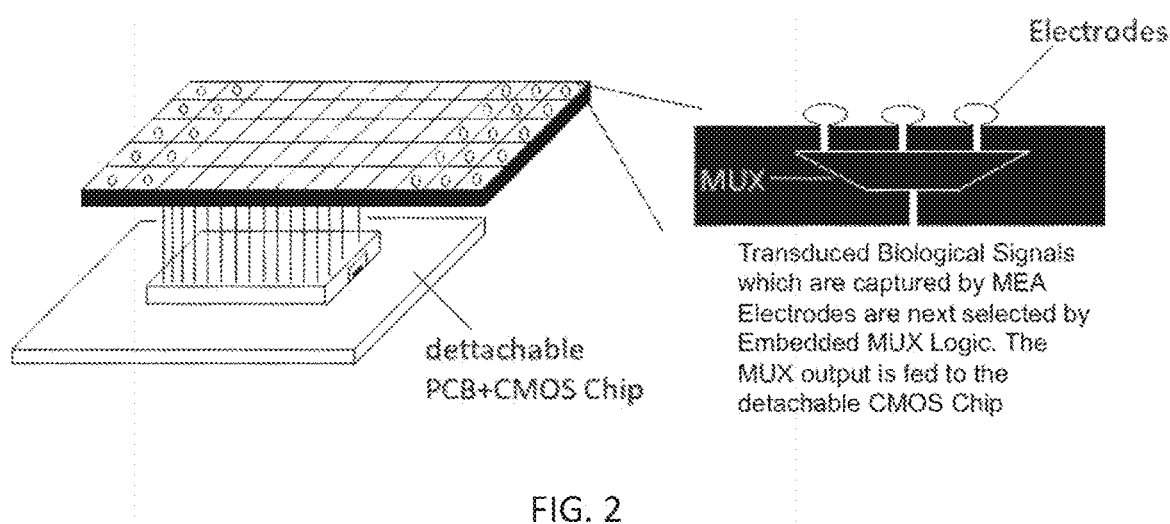
FIG. 2 shows stacking of an MEA chip through electrodes with an embedded MUX logic, on top of CMOS chip accessed through a bottom side of the MEA chip.

Provided herein is a novel architecture to stack a silicon or printed circuit board MEA chip through electrode vias with an embedded MUX Logic, on top of a CMOS chip accessed through the bottom of the MEA chip (See FIG. 2). These electrode outputs may be stacked on electrical pins, which may be in turn connected to the CMOS chip. The electrical pins may be shielded to mitigate parasitic currents and noise. Due to the increase in the available active area of electrodes on the top surface of the MEA, made possible by 3D stacking, the number of electrodes which may be fabricated, for example, on an about 10×10 mm2 chip area with each electrode footprint about 10×10 um2 (inter-electrode pitch of 5 um), is >about 400,000, with standard micro-electro-mechanical systems (MEMS) lithography technology. On a larger MEA chip (area of about 50×50 mm2) the number of active electrodes may be >about 1,000,000, which can be sub-grouped into families of about 10 to about 1000 electrodes each to form about 1000 to about 100,000 groups of electrodes. Apart from the above feature of larger number of electrodes, due to the novel 3D stacking architecture, the second advantage may be removal, disposal and replacement of the MEA chip after cell longevity is exhausted, while the rest of the device components such as CMOS chip and other electrical components, can be re-used. In addition to this, a novel CMOS chip underlying the MEA chip may be designed to include basic signal processing components such as filters, amplifiers, ADC (analog-to-digital converter), DAC (digital-to-analog converter) together. Computation may take place directly on the chip.

Another embodiment of the above is that the MEA may be stacked directly on top a printed circuit board ("PCB"), which is again connected to the electrode outputs accessed from the bottom side of the MEA.

III. MEA Level

A device comprises a microelectrode array comprising a substrate comprising microelectrodes communicating with the surface of the substrate and one or more MUX circuits integrated with the MEA. Each MUX circuit is electrically connected to a plurality of the microelectrodes. The MEA is configured to receive electrical signals from cells placed on the surface of the substrate and an electrical connection with the microelectrodes.

MUX circuits can be integrated circuits. MUX circuits can be integrated with the MEA by, for example, insertion into an aperture in the MEA substrate and by forming electrical connections between microelectrodes and MUX inputs. Electrical connections can be made, for example, by soldering electrical traces in the MEA with the MUX inputs.

The device can comprise one or more containers, such as open wells or closed compartments are provided on the substrate surface. The wells or compartments define spaces that are enclosed, in part by the substrate surface and, thereby, in electrical contact with the microelectrodes. The number of wells or compartments can be one or a plurality. A plurality can include at least two, at least four, at least 10, at least 50, at least 100, at least 500, or at least 1000 wells or compartments. Wells or compartments can be made of a polymer substrate comprising bores that partially define the wells or compartments and which is affixed to the MEA surface. Wells can be covered by a layer of material, such as plastic or glass, to form closed compartments.

Figure 4:
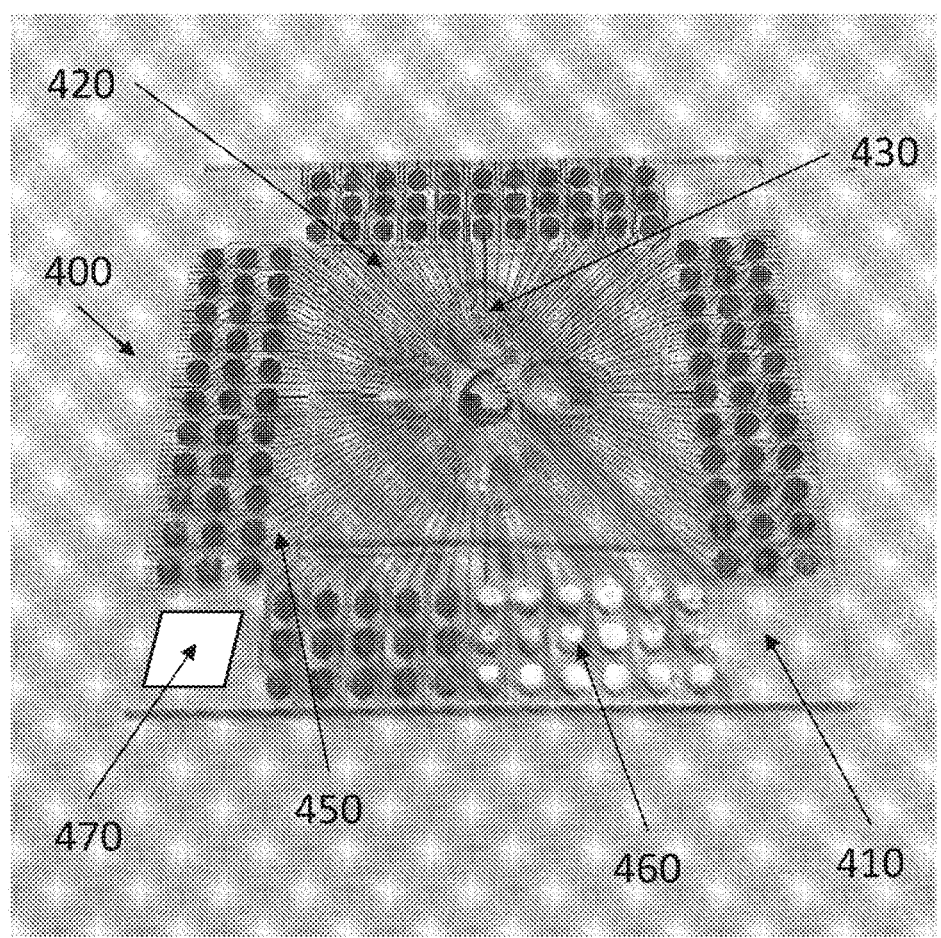
FIG. 4 shows and exemplary MEA chip with wells.

Referring to FIG. 4, in certain embodiments device 400 comprises substrate 410. On the substrate surface is well block 420 defining wells 430. Microelectrodes 450 terminate on the substrate surface in the wells and in electrical pads 460. MUX 470 is integrated into the device.

Cells to be included in wells or compartments of the device can be any cells that produce an electrical signal upon stimulation. In certain embodiments, cells comprise neurons. In other embodiments the cells express olfactory receptors. Olfactory receptors are transmembrane proteins that transmit a signal into the cell when they bind with a chemical stimulant. Different olfactory receptors can bind to different chemical entities. Several hundred human olfactory receptors are known and functioning olfactory receptors can be produced through mutation. Such cells can be produced through recombinant DNA technology. For example, Cells can be recombinant cells engineered to express receptors, such as olfactory receptors or genetically engineered receptors that bind extracellular ligands, to transduce signals from olfactory receptors stimulated by volatile organic compounds to ultimately produce an electrical signal that can be detected by a system as disclosed herein.

See, for example, International patent publications WO 2017/015148, WO 2018/081657, WO 2018/208332, WO 2018/237302, and WO 2019/040910.

IV. CMOS Level

The recorded spike signals received from electrodes may be processed in analog & mixed signal chip block. The analog & mixed chip block may contain ADC, DAC, one or more filter, one or more amplifiers, analog MUX and other signal processing components. The cell, e.g., neuron, stimulation block may be part of the chip, where we can give digital input, which later can be converted to analog signal and pass to one or more cells, e.g., neurons, through electrodes. There may be control over which electrode to record or to stimulate. Sensors like temperature, humidity etc. may be integrated with this chip.

The processed signal from analog & mixed signal chip block is in digital domain and fed to the digital chip block. The digital block chip may be a dedicated digital processor. The processor can do many different computations. It can do spike signal sorting based on an algorithm. The machine learning, artificial intelligence, deep learning and neural network algorithms may be implemented on silicon, where one can analyze a cell's, e.g., a neuron's, behavior patterns for different stimuli (chemical, mechanical, optical, electrical, thermal, electromagnetic, etc.) cell, e.g., neuron, firing rate, chemical detection, storing this previous pattern to make better prediction in future. The novelty of this approach may be to eliminate PC dependency wherein data transferred over cable interface is analyzed by PC software. Since this processor may eliminate the dependency on PC, the computation through this processor may be much faster than PC software and it may make this device portable (one can put in on the wall without PC or put on the drone). Additionally, the chip may be designed to carry out specific computations vs. general computation of the PC.

The processor may be capable of communication with outside world through USB, USB+C interface, serial peripheral interface (SPI) interface, universal asynchronous receiver-transmitter (UART) interface, PCI interface. By these interfaces we can connect FPGA or PC to the device and perform post signal processing on PC. By embedding Wi-Fi module with digital processor, data can be transferred directly to cloud-based database which may eliminate a person presence and the data can be monitored from around the world. The person can also communicate with Wi-Fi module, which can talk to digital processor via cloud by using secured communication protocol.

Figure 3:
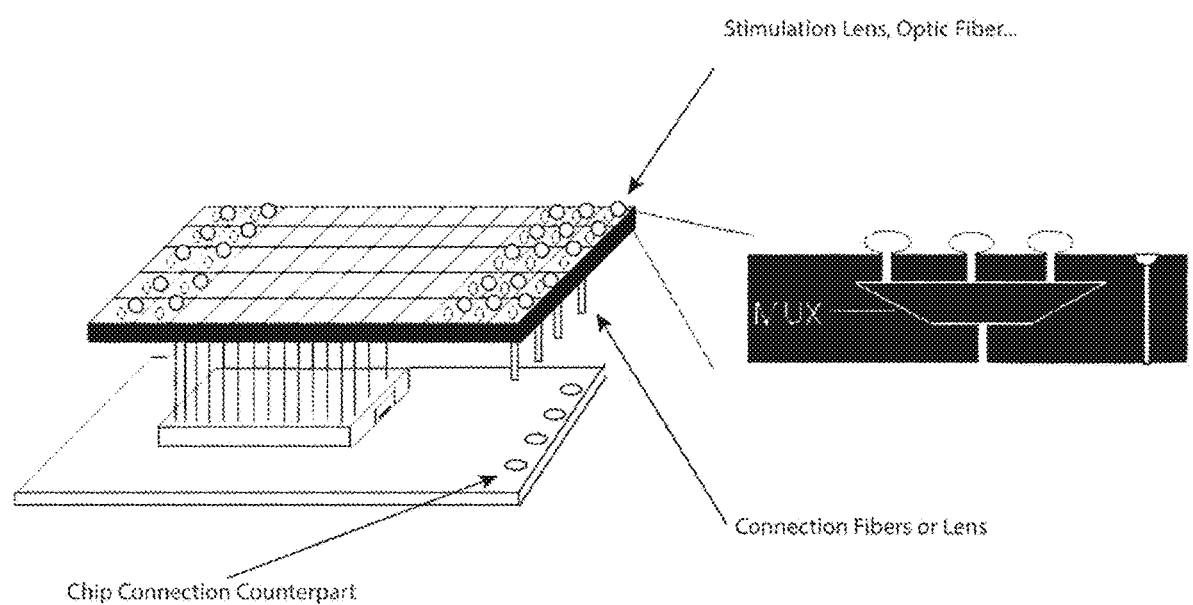
FIG. 3 shows an interfacing component configured as an optical element (such as a fiber or lens) which thereby associates an MEA chip with a CMOS chip.

The chip, such as a passive chip, can support one or more of the following: optical elements implemented with MEMS lenses; integrated secondary optical fibers; optical pathways embedded within the chip; or any combination thereof (See FIG. 3). An exposed part of an optical fiber may stimulate cell, e.g., neuron, positioning adjacent an electrode, such as sitting atop an electrode.

Additionally, optical pathways associated with an MEA substrate, such as positioned inside or atop the MEA substrate, may have passive optical switches so that no matter how many exposed light sources sit atop the MEA, the connection to the CMOS MEA or the electronics part may be significantly minimized. An MEA substrate may be configured to be a passive MEA substrate.

A connection to the MEA, such as a passive low cost MEA, can be accomplished by optical elements such as lenses, fibers or even GRIN lenses—which in some cases may be coupled to a CMOS chip with pressure or other clasping mechanisms which ensure that alignment may be achieved (See FIG. 3).

An MEA substrate may be configured to be associated to a CMOS substrate via electrical pins or optical elements, or a combination thereof. An MEA substrate may be configured to be removable or separable from a CMOS substrate. An MEA substrate may be associated with a CMOS substrate in a linear stacking configuration.

V. Methods of Use

Systems as disclosed herein are useful in collecting and processing electrical signals produced by cells in contact with a microelectrode array. Methods can involve culturing cells on the surface of the microelectrode array. For example, the cells can be cultured in culture medium deposited in containers, such as wells or compartments, in electrical contact with the microelectrodes. A number of microelectrodes on the array can be sufficient such that a signal from each cultured cell can be detected by one or a plurality of microelectrodes. That is to say, detection can be redundant. The MUX circuit allows efficient transmission of signals from each microelectrode to the microprocessor with which the device is engaged. This process can involve analog-to-digital conversion of the signal.

In certain embodiments different cell types, each cell type being excitable by different stimulus, can be used on the array. In this way, different stimuli can be detected. For example, each of a plurality of different containers on the microelectrode array can comprise cells in which cells in each container express a different olfactory receptor. A test sample, such as a gas (e.g., air) or liquid can be put into contact with cells in each compartment. If the sample contains a chemical compound that is recognized by an olfactory receptor in a cell in a particular container those cells will generate an electrical signal which can be detected by microelectrodes in a contact with though cells. The signal is transmitted to the processor and processed to determine, for example, the compartment and, therefore, olfactory receptor, that is stimulated, as well as the intensity of signal. The intensity of the signal may indicate the concentration of the chemical compound in the sample.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The phrase "at least one" includes "one or more", "one or a plurality" and "a plurality". The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

All publications, patents, and patent applications mentioned in this specification are herein incorporated by reference to the same extent as if each individual publication, patent, or patent application was specifically and individually indicated to be incorporated by reference.

The invention claimed is:

1. A microelectrode array system comprising:
    a microelectrode array (MEA) component including a plurality of exposed microelectrodes adapted to receive electrical signals from, or to transmit electrical signals to, living cells, the microelectrode array including an embedded multiplexed logic circuit (MUX);
    a complementary metal-oxide-semiconductor (CMOS) component electrically connected to the MEA component;
    wherein the MEA component and the CMOS component are separable from each other;
    the MEA component comprises one or more living cells which express odorant receptors, and the system is configured to perform odorant detection.

2. The system of claim 1 wherein the microelectrodes of the MEA component are associated with an interfacing component via the MUX logic circuit, and wherein the interfacing component is also associated with the CMOS component.

3. The system of claim 1 further comprising an interfacing component configured to operably connect the MEA component with the CMOS component.

4. The system of claim 3 wherein the interfacing component comprises an electrical pin, an optical element, or a combination thereof.

5. The system of claim 1 wherein the MEA component comprises at least 1,000 microelectrodes.

6. The system of claim 1 wherein the MUX is configured to consolidate inputs from the plurality of microelectrodes into a reduced number of outputs.

7. A microelectrode array system comprising:
    a microelectrode array (MEA) component including a plurality of exposed microelectrodes adapted to receive electrical signals from, or to transmit electrical signals to, living cells, the microelectrode array including an embedded multiplexed logic circuit (MUX);
    a complementary metal-oxide-semiconductor (CMOS) component electrically connected to the MEA component;
    wherein the MEA component and the CMOS component are separable from each other, in a stacked arrangement, and a surface of the MEA component is positioned adjacent a surface of the CMOS component.

8. The system of claim 7 wherein the living cells express odorant receptors, and the system is configured to perform odorant detection.

9. A microelectrode array device comprising:
    a microelectrode array (MEA) component comprising a plurality of microelectrodes in electrical contact with a surface of a substrate;
    a plurality of compartments formed on or in the surface of the substrate, each compartment comprising a space in electrical contact with one or more of the plurality of microelectrodes;
    one or more multiplexed (MUX) logic circuits each comprising, (1) as inputs, electrical connections with each of a plurality of the microelectrodes, (2) one or more outputs, and (3) a switch that selects between several input signals and forwards a selected input signal to an output line, wherein the total number of outputs is fewer than the total number of microelectrodes;
    a plurality of living cells in each compartment, wherein the living cells express olfactory receptors.

10. The device of claim 9 further including an electrical interface configured to engage the one or more outputs, and a microprocessor, wherein the interface transmits signals from the one or more outputs to the microprocessor.

11. A method comprising:
    engaging a first device to an electrical interface configured to transmit electrical signals received from the outputs of the first device to a microprocessor, the first device comprising an MEA component including a plurality of microelectrodes in electrical contact with a plurality of compartments on or in a substrate, respectively, the compartments containing living cells of the type that express odorant receptors and produce an electrical signal when exposed to a stimulus, the first device further comprising one or more multiplexed (MUX) logic circuits adapted to consolidate inputs from the plurality of microelectrodes into a reduced number of outputs to the microprocessor;
    processing the electrical signals from the outputs via the microprocessor; and
    disengaging the first device from the electrical interface.

12. The method of claim 11 wherein processing comprises determining an intensity of the electrical signals.

13. The method of claim 11 wherein the living cells detect one or more volatile compounds.

14. The method of claim 11 further including contacting the living cells with a gas or liquid test sample.

* * * * *